United States Patent [19]

Taylor

[11] Patent Number: 4,552,728

[45] Date of Patent: Nov. 12, 1985

[54] DECONTAMINATION APPARATUS

[75] Inventor: William R. Taylor, Lugarno, Australia

[73] Assignee: Hal Johnston Pty. Limited, New South Wales, Australia

[21] Appl. No.: 455,429

[22] Filed: Jan. 3, 1983

Related U.S. Application Data

[63] Continuation of Ser. No. 262,453, May 11, 1981, abandoned.

[51] Int. Cl.⁴ ............................................. A61L 9/00
[52] U.S. Cl. .................................. 422/300; 422/297; 422/307; 134/166 R; 134/200
[58] Field of Search .................. 422/297, 292, 300, 6, 422/305, 307; 134/166 R, 170, 200, 22.14

[56] References Cited

U.S. PATENT DOCUMENTS

| | | | |
|---|---|---|---|
| 1,625,202 | 4/1927 | Gindiek | 422/300 |
| 2,225,817 | 12/1940 | Arnold | 422/300 |
| 3,070,104 | 12/1962 | Faust | 134/70 |
| 3,478,758 | 11/1969 | Davies | 422/300 |
| 3,587,597 | 6/1971 | Courtney et al. | 134/170 |
| 3,881,503 | 5/1975 | Fox et al. | |
| 4,354,514 | 10/1982 | Sundheimer et al. | |

FOREIGN PATENT DOCUMENTS

| | | | |
|---|---|---|---|
| 2600088 | 7/1976 | Fed. Rep. of Germany | 134/170 |
| 2712020 | 9/1978 | Fed. Rep. of Germany | 422/300 |
| 1168035 | 10/1969 | United Kingdom | |

*Primary Examiner*—Bernard Nozick
*Attorney, Agent, or Firm*—Barnes & Thornburg

[57] ABSTRACT

A decontamination apparatus comprising a decontamination chamber for holding and treating articles to be decontaminated, a lid arranged to provide access to the chamber for installing articles to be decontaminated and for removal therefrom, an ancilliary chamber containing decontamination fluid supply and control means for the decontamination chamber, the decontamination chamber comprising at least two regions so as to provide one relatively deep region wherein elongate articles such as elongate flexible breathing tubes can be suspended, and a second relatively shallow region wherein smaller articles such as breathing masks can be held or suspended, at least a lower portion of the deep region being defined by a trough into which decontaminating fluid can drain from the decontamination chamber, the decontamination chamber further including support devices for holding articles to be decontaminated, spray devices arranged in both decontamination regions for spraying decontamination fluid into or over articles arranged in the decontamination chamber, and distributing means comprising a network of pipes and manifolds for transferring decontamination fluid from the trough to the spray devices.

12 Claims, 10 Drawing Figures

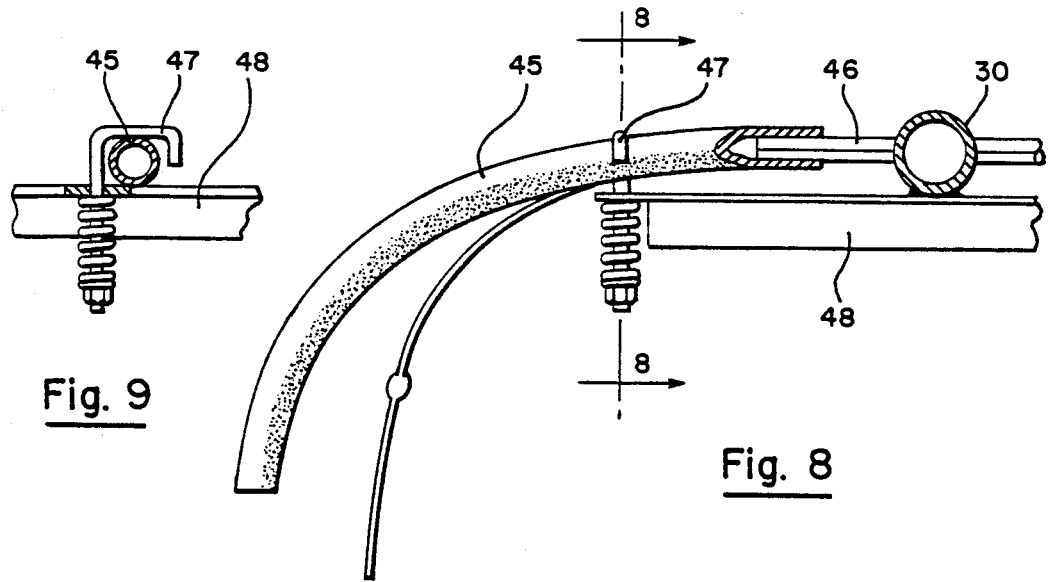
Fig. 9
Fig. 8
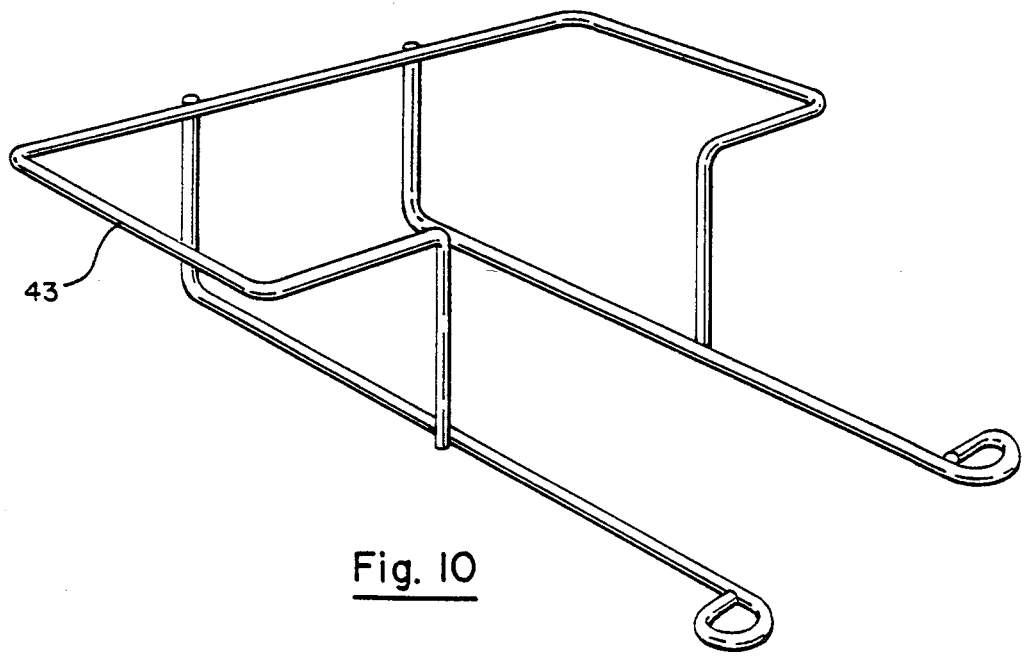
Fig. 10

DECONTAMINATION APPARATUS

This is a continuation of application Ser. No. 262,453 filed May 11, 1981 now abandoned.

The present invention provides a decontamination apparatus suitable for treating and decontaminating hospital equipment such as rubber or plastics breathing tubes, bags and fittings. It will be appreciated, however, that the invention is not limited to this particular application.

In the past, considerable difficulty has been achieved in properly sterlizing rubber or plastics items such as flexible breathing tubes. It is an object of the present invention to provide an improved means for decontaminating equipment such as this in a compact and efficient manner.

Accordingly, the present invention provides a decontamination apparatus comprising a decontamination apparatus comprising a decontamination chamber for holding and treating articles to be decontaminated, a lid arranged to provide access to said chamber for installing articles to be decontaminated and for removal therefrom, an ancilliary chamber containing decontamination fluid supply and control means for said decontamination chamber, said decontamination chamber comprising at least two regions so as to provide one relatively deep region wherein elongate articles such as elongate flexible breathing tubes can be suspended, and a second relatively shallow region wherein smaller articles such as breathing masks can be held or suspended, at least a lower portion of said deep region being defined by a trough into which decontaminating fluid can drain from said decontamination chamber, said decontamination chamber further including support devices for holding articles to be decontaminated, spray devices arranged in both decontamination regions for spraying decontamination fluid into or over articles arranged in the decontamination chamber, and distributing means comprising a network of pipes and manifolds for transferring decontamination fluid from said trough to said spray devices.

A preferred embodiment of the invention will now be described, by way of example only, with reference to the accompanying drawings in which:

FIG. 8 is an enlarged sectional view taken on line 5—5 of FIG. 1 but showing an alternative form of hose clamp for smaller breathing tubes.

FIG. 9 is a view taken on line 8—8 of FIG. 8.

FIG. 10 is an enlarged perspective view of tray positioned within the decontamination chamber.

Figure 1:
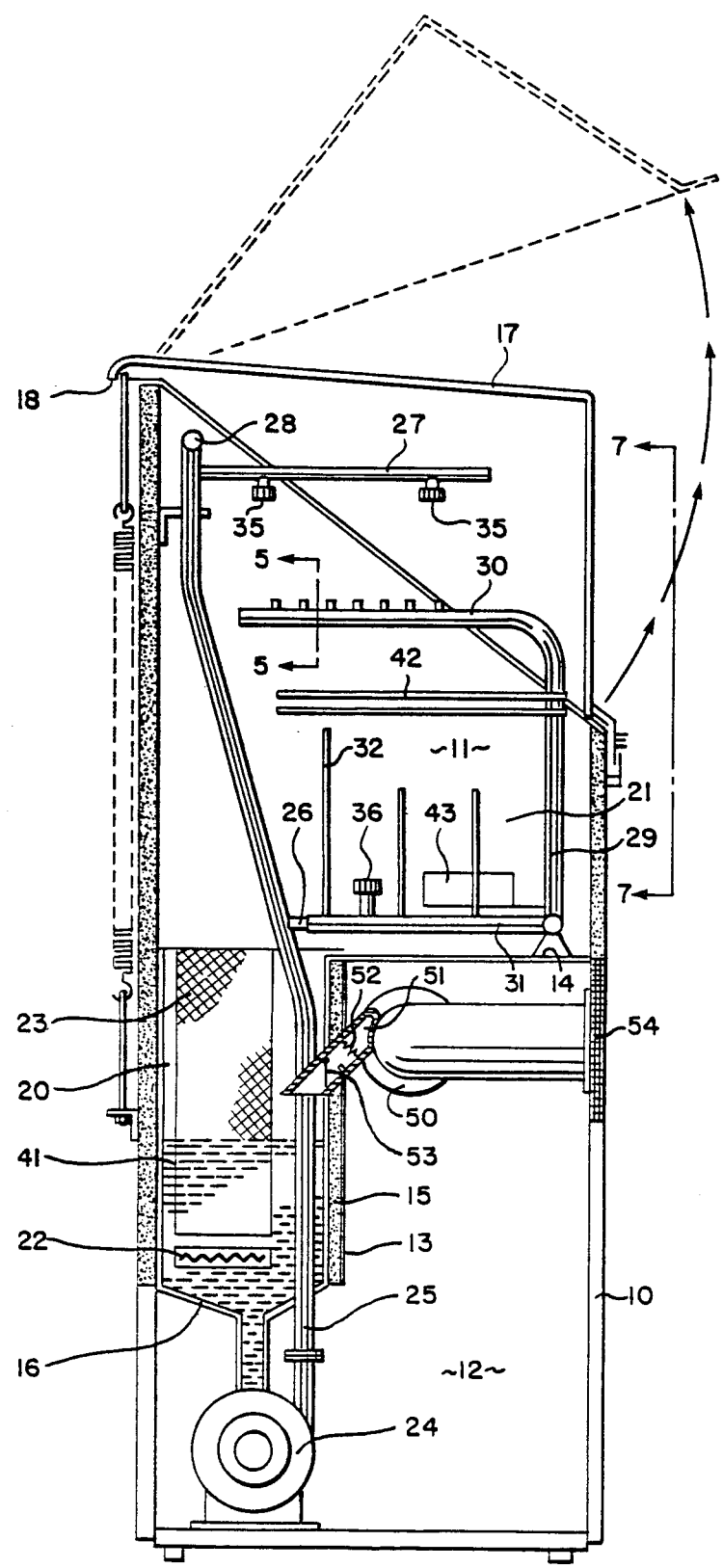
FIG. 1 is a sectional side elevation of a decontamination apparatus according to the invention.

Referring to the drawings, the decontamination apparatus comprises a vertically upstanding cabinet 10 divided into a decontamination chamber 11 and an ancilliary chamber 12 by a stepped wall 13, having a horizontal upper shelf portion 14, a vertical centre step 15 and a floor 16. The decontamination chamber 11 is accessible by a hinged lid 17 which is rotatable about an axis 18 as shown to permit easy access to the chamber.

It can be seen that the arrangement provides a decontamination chamber having two identifiable regions—a relatively deep rear section 20 extending from the underside of the hinged lid 17 to the floor 16 and a relatively shallow forward section 21 extending above the upper shelf portion 14. The rear section 20 contains a heater element 22 located beneath a pair of removable gauze baskets 23.

The object of the dual nature of the decontamination chamber is to provide for treatment of long hoses or other elongate articles in the rear section simultaneously with the treatment of smaller articles in the remainder of the chamber. To this end, the apparatus is provided with a network of fluid supply pipes extending from a pump 24 located in the lower part of the ancilliary chamber 12 so as to draw fluid from the decontamination chamber during operation of the apparatus.

Figure 6:
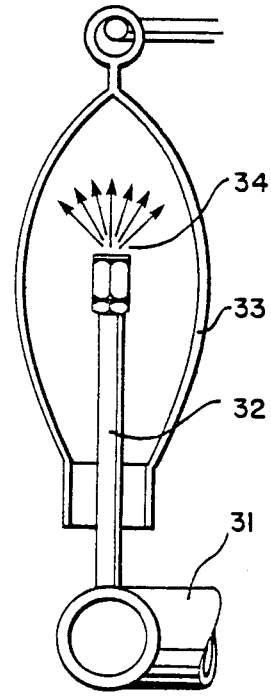
FIG. 6 is a sectional view showing a breathing bag in position on the apparatus.

The fluid supply network extends from the pump 24 through a vertical supply pipe 25 to a spiggot 26 and two horizontal manifolds 27 and 28. A removable spraying assembly 29 engages with the spiggot 26 as shown so that water can flow from the pipe 25 to an intermediate manifold 31 which supports a plurality of vertical spraying pipes 32. The pipes 32 are adapted to receive breathing bags 33 as best shown in FIG. 6 and are provided with a plurality of spray holes 34 for directing fluid into the interior of the bags. The entire assembly 29 can be removed from chamber 11 for loading and unloading, as well as to provide access to the removable baskets 23.

Figure 2:
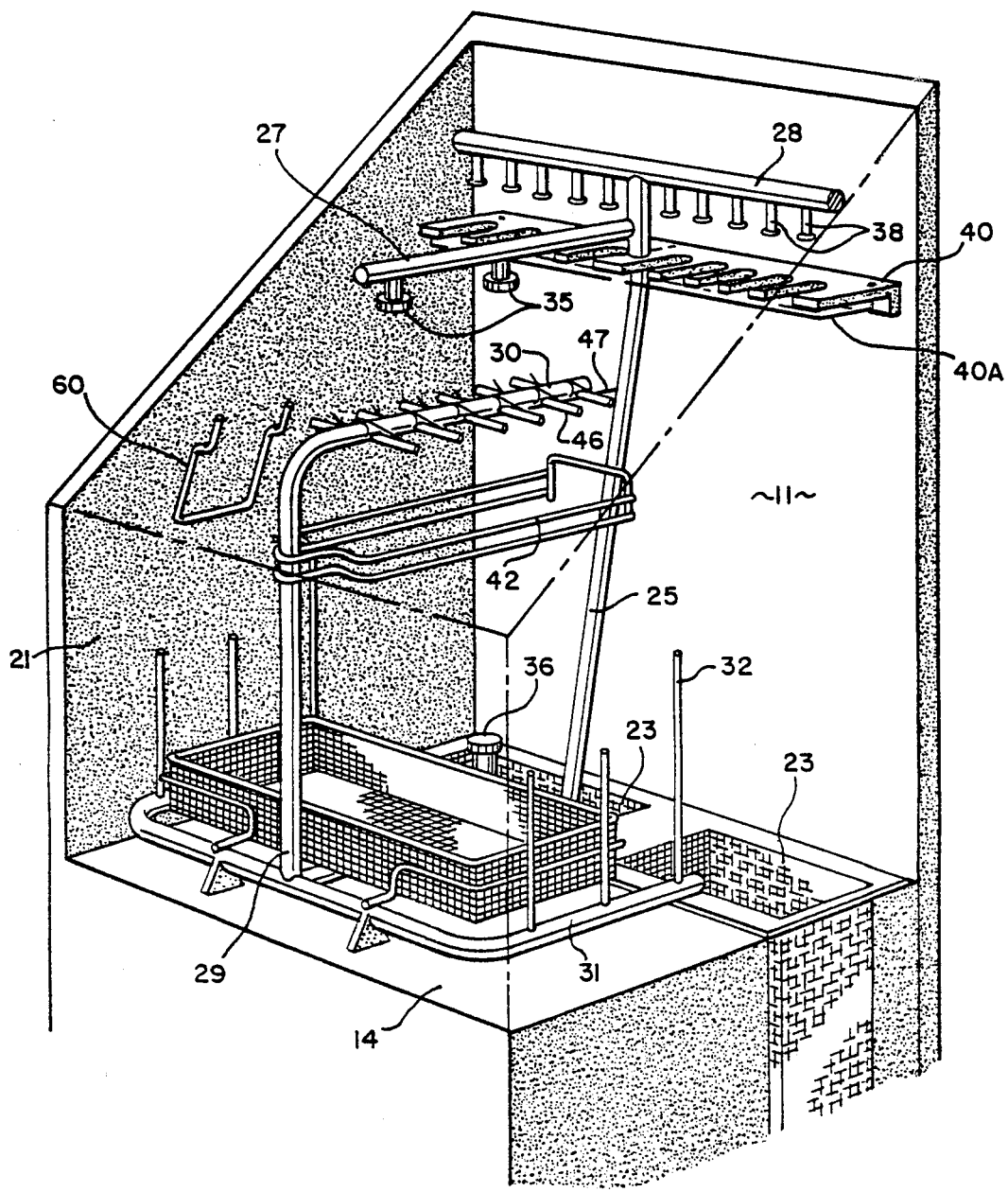
FIG. 2 is a perspective view showing the washing chamber of the apparatus shown in FIG. 1.
Figure 3:
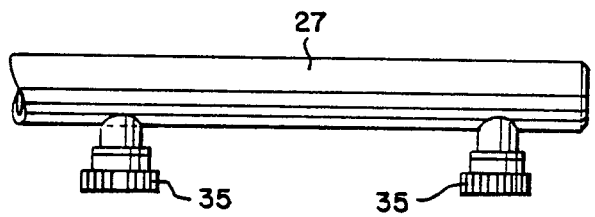
FIG. 3 is an enlarged view of part of the spraying apparatus shown in FIG. 1.
Figure 5:
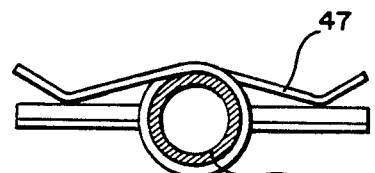
FIG. 5 is an enlarged section taken on line 5—5 of FIG. 1 showing a pair of hose clamps for smaller breathing tubes.
Figure 7:
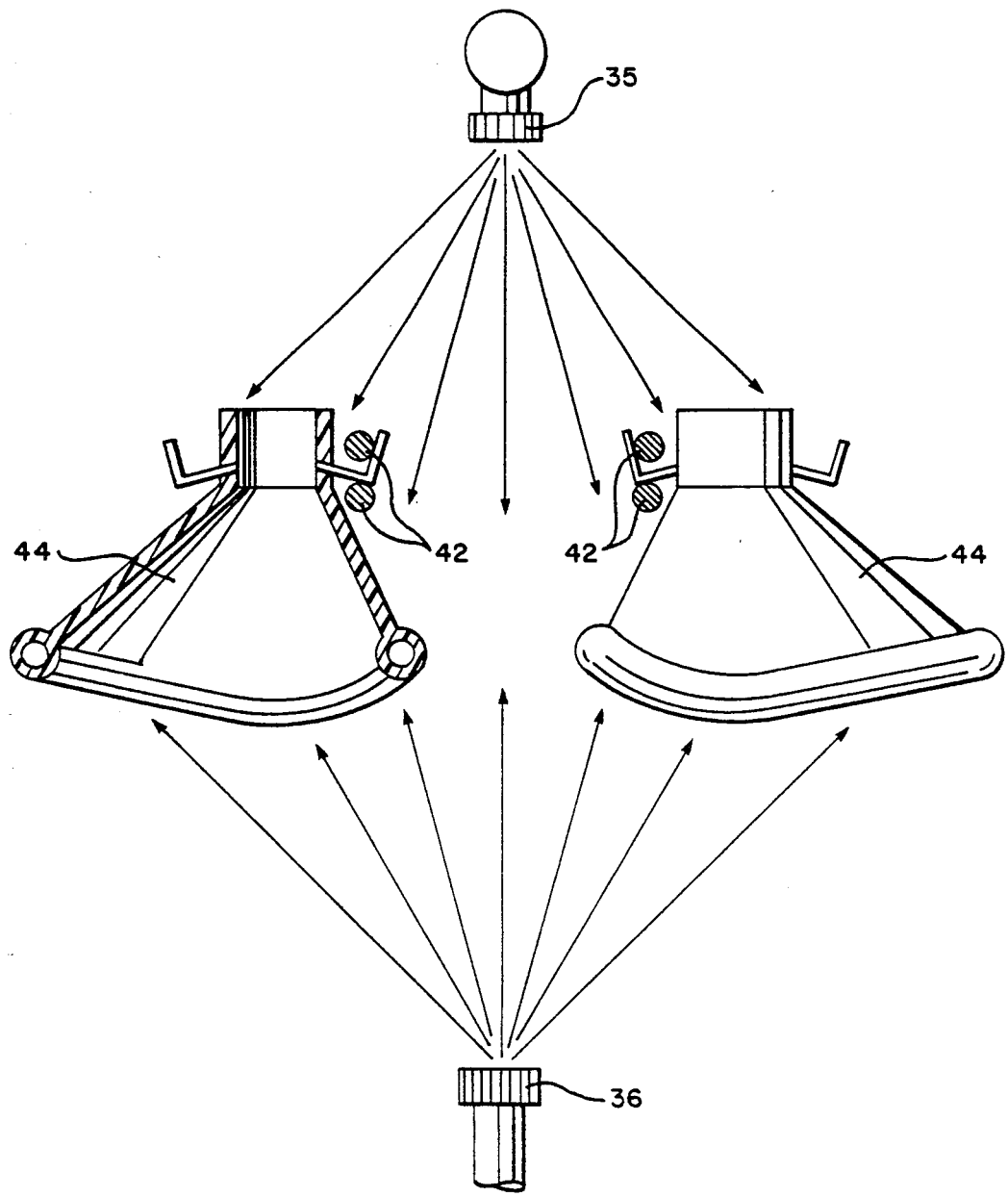
FIG. 7 is a sectional view taken generally on line 7—7 of FIG. 1 showing a pair of masks positioned on rails supported within the washing chamber between upper and lower jets.

The manifold 27 communicates with two downwardly directed nozzles 35 while the spiggot 26 feeds at least one upwardly directed nozzle 36 as best shown in FIGS. 2, 3 and 7. These nozzles direct decontamination fluid in a spray pattern over articles positioned in the upper part of the decontamination chamber.

Figure 4:
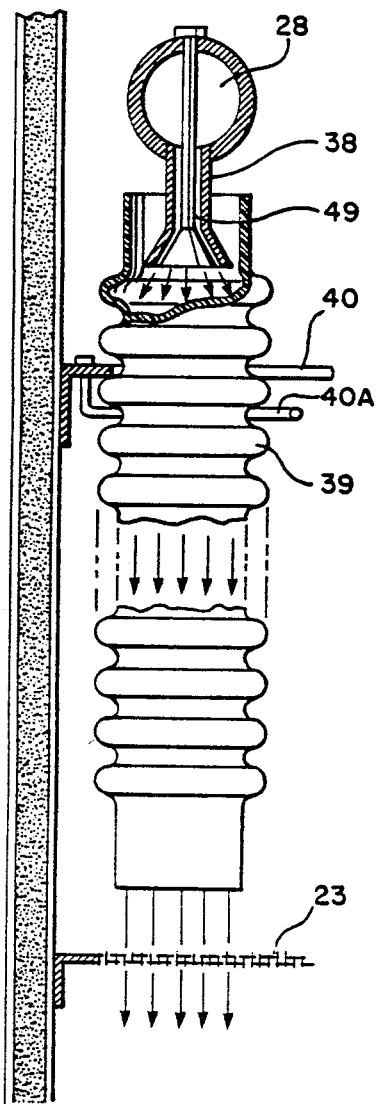
FIG. 4 is a partly sectioned view showing a breathing tube in position within the apparatus.

The upper manifold 28 is provided with a plurality of downwardly directed nozzles 38 for supplying decontamination fluid into the interior of elongate breathing tubes 39 vertically presented to the nozzles 38 and supported by a slotted rack 40 and hinged gate 40A. As best shown in FIG. 4, each nozzle 38 includes an adjustable jet rod 49 for regulating the spray within the tubes. In operation, the lowermost ends of the tubes 39 are contained by the baskets 23 and extend into the fluid 41 at the bottom of the chamber 11.

The decontamination chamber is also provided with racks such as 42, 43 and 60 to support articles such as masks 44 within the upper portion of the chamber as best shown in FIG. 7.

Smaller breathing tubes 45 are accommodated by the intermediate manifold 30. The manifold 30 supports a plurality of horizontally extending nozzles 46 over which the upper end of the tubes 45 can be secured by spring loaded retension clips 47. FIGS. 8 and 9 show an alternative arrangement where retention hooks 47 are employed, supported by brackets 48.

With the various articles to be decontaminated located within the decontamination chamber and the lid closed, the decontamination cycle, once initiated, is controlled by conventional means. The apparatus admits water at 60° C. to the level shown for a preliminary wash cycle. The preliminary wash continues for a predetermined time during which a suitable amount of detergent or other sterlizing medium is added automatically to the water. At the completion of the preliminary washing cycle, the system replaces the used fluid with fresh water at 60° C. and heats it to a higher temperature of, say, 75° C. and then performs a rinsing or sanitizing cycle of predetermined length.

At the completion of the sanitizing cycle, the water is removed and a fan drying cycle commences using filtered air supplied to the lower part of the decontamination chamber 11 by one or more fans 50 each provided with an outlet duct 51 containing a heating element 52 and a one way flap valve 53 for preventing water entering the fan during the decontamination process. The air is filtered by removable filter elements 54. The operation of the apparatus is such that it is automatically deactivated if the lid is opened at any time during the cycle.

Although the invention has been described with reference to a specific example, it will be appreciated by those skilled in the art, that it may be embodied in many other forms.

I claim:

1. A decontamination apparatus comprising a decontamination chamber for holding and treating articles to be decontaminated, a lid arranged to provide access to said chamber for installing articles to be decontaminated and for removal therefrom, an ancillary chamber containing decontamination fluid supply and control means for said decontamination chamber, said decontamination chamber comprising at least two regions so as to provide one relatively deep region at the rear of said apparatus wherein elongate breathing tubes can be suspended vertically to provide complete drainage, and a second relatively shallow region at the front of said apparatus wherein smaller articles such as breathing masks can be held or suspended, at least a lower portion of said deep region being defined by a trough into which decontaminating fluid can drain from said decontamination chamber, said decontamination chamber further including support devices for holding articles to be decontaminated, spray devices defined by a plurality of downwardly directed nozzles for supplying decontamination fluid into the interior of said elongate breathing tubes, each nozzle including an adjustable jet rod for regulating the spray within said tubes, said spray devices arranged in both decontamination regions for spraying decontamination fluid into or over articles arranged in the decontamination chamber, and distributing means comprising a network of pipes and manifolds for transferring decontamination fluid from said trough to said spray devices, the spray devices and distributing means provided in said shallow region of said decontamination chamber being defined by a removable spraying assembly, the distributing means for said elongate breathing tubes including a manifold located in the upper portion of said deep region of said decontamination chamber, said manifold being provided with said spray devices.

2. A decontamination apparatus according to claim 1 in which at least one removable fluid permeable basket is located in said trough, said decontaminating fluid draining therethrough.

3. A decontamination apparatus according to claim 1 wherein said ancillary chamber contains heater means for supplying drying air to said decontamination chamber.

4. A decontamination apparatus according to claim 1 wherein said trough contains a heating element for heating decontamination fluid therein.

5. A decontamination apparatus according to claim 1 wherein said removable assembly includes a manifold supporting a plurality of vertically disposed spraying pipes adapted for receiving articles such as breathing bags thereon, each pipe being provided with a plurality of spray holes for directing fluid into an article received thereon.

6. A decontamination apparatus according to claim 5 wherein said removable spraying assembly releasably engages a spigot extending outwardly from a vertically extending supply pipe.

7. A decontamination apparatus according to claim 5 wherein said removable spraying assembly includes a second manifold provided with a plurality of horizontally extending nozzles over which the upper ends of tubular articles can be secured.

8. A decontamination apparatus comprising a decontamination chamber for holding and treating articles to be decontaminated, a lid arranged to provide access to said chamber for installing articles to be decontaminated and for removal therefrom, an ancillary chamber containing decontamination fluid supply and control means for said decontamination chamber, said decontamination chamber comprising at least two regions so as to provide one relatively deep region at the rear of said apparatus wherein elongate articles such as elongate flexible breathing tubes can be suspended vertically to provide complete drainage, and a second relatively shallow region at the front of said apparatus wherein smaller articles such as breathing masks can be held or suspended, at least a lower portion of said deep region being defined by a trough into which decontaminating fluid can drain from said decontamination chamber, said decontamination chamber further including support devices for holding articles to be decontaminated, spray devices arranged in both decontamination regions for spraying decontamination fluid into or over articles arranged in the decontamination chamber, the support devices for elongate articles including a slotted rack and hinged gate from which said elongate articles can be suspended, said slotted rack and hinged gate being located below said spray devices, and distributing means comprising a network of pipes and manifolds for transferring decontamination fluid from said trough to said spray devices, the spray devices and distributing means provided in said shallow region of said decontamination chamber being defined by a removable spraying assembly, the distributing means for said elongate articles including a manifold located in the upper portion of said deep region of said decontamination chamber, said manifold being provided with said spray devices.

9. A decontamination apparatus comprising a decontamination chamber for holding and treating articles to be decontaminated, a lid arranged to provide access to said chamber for installing articles to be decontaminated and for removal therefrom, an ancillary chamber containing decontamination fluid supply and control means for said decontamination chamber, said decontamination chamber comprising at least two regions so as to provide one relatively deep region at the rear of said apparatus wherein elongate articles such as elongate flexible breathing tubes can be suspended vertically to provide complete drainage, and a second relatively shallow region at the front of said apparatus wherein smaller articles such as breathing masks can be held or suspended, at least a lower portion of said deep region being defined by a trough into which decontaminating fluid can drain from said decontamination chamber, said decontamination chamber further including support devices for holding articles to be decontaminated, spray devices arranged in both decontamination regions for spraying decontamination fluid into or over articles arranged in the decontamination chamber, and distributing means comprising a network of pipes and manifolds for transferring decontamination fluid from said trough to said spray devices, the spray devices and distributing means provided in said shallow region of said decontamination chamber being defined by a removable spraying assembly including a manifold supporting a plurality of vertically disposed spraying pipes adapted for receiving articles such as breathing bags thereon, each pipe being provided with a plurality of spray holes for directing fluid into an article received thereon, a second manifold provided with a plurality of horizontally extending nozzles over which the upper ends of tubular articles can be secured, and spring-loaded retention clips for securing the upper ends of tubular articles, the distributing means for said elongate articles including a manifold located in the upper portion of said deep region of said decontamination chamber, said manifold being provided with said spray devices.

10. A decontamination apparatus comprising a decontamination chamber for holding and treating articles to be decontaminated, a lid arranged to provide access to said chamber for installing articles to be decontaminated and for removal therefrom, an ancillary chamber containing decontamination fluid supply and control means for said decontamination chamber, said decontamination chamber comprising at least two regions so as to provide one relatively deep region at the rear of said apparatus wherein elongate articles such as elongate flexible breathing tubes can be suspended vertically to provide complete drainage, and a second relatively shallow region at the front of said apparatus wherein smaller articles such as breathing masks can be held or suspended, at least a lower portion of said deep region being defined by a trough into which decontaminating fluid can drain from said decontamination chamber, said decontamination chamber further including support devices for holding articles to be decontaminated, spray devices arranged in both decontamination regions for spraying decontamination fluid into or over articles arranged in the decontamination chamber, and distributing means comprising a network of pipes and manifolds for transferring decontamination fluid from said trough to said spray devices, the spray devices and distributing means provided in said shallow region of said decontamination chamber being defined by a removable spraying assembly including a manifold supporting a plurality of vertically disposed spraying pipes adapted for receiving articles such as breathing bags thereon, each pipe provided with a plurality of spray holes for directing fluid into an article received thereon, a second manifold provided with a plurality of horizontally extending nozzles over which the upper ends of tubular articles can be secured, and retention hooks and brackets for securing the upper ends of tubular articles, the upper ends of the tubular articles being held therebetween, the distributing means for said elongate articles including a manifold located in the upper portion of said deep region of said decontamination chamber, said manifold being provided with said spray devices.

11. A decontamination apparatus comprising a decontamination chamber for holding and treating articles to be decontaminated, a lid arranged to provide access to said chamber for installing articles to be decontaminated and for removal therefrom, the lid having a top portion which slopes downwardly towards the front of said apparatus when in the closed position, an ancillary chamber containing decontamination fluid supply and control means for said decontamination chamber, said decontamination chamber comprising at least two regions so as to provide one relatively deep region at the rear of said apparatus wherein elongate articles such as elongate flexible breathing tubes can be suspended vertically to provide complete drainage, and a second relatively shallow region at the front of said apparatus wherein smaller articles such as breathing masks can be held or suspended, at least a lower portion of said deep region being defined by a trough into which decontaminating fluid can drain from said decontamination chamber, said decontamination chamber further including support devices for holding articles to be decontaminated, spray devices arranged in both decontamination regions for spraying decontamination fluid into or over articles arranged in the decontamination chamber, and distributing means comprising a network of pipes and manifolds for transferring decontamination fluid from said trough to said spray devices, the spray devices and distributing means provided in said shallow region of said decontamination chamber being defined by a removable spraying assembly, the distributing means for said elongate articles including a manifold located in the upper portion of said deep region of said decontamination chamber, said manifold being provided with said spray devices.

12. A decontamination apparatus according to claim 11 wherein said lid is hinged for rotation about a horizontal axis located at the rear of said apparatus.

* * * * *